United States Patent
Answine

(10) Patent No.: US 10,507,299 B2
(45) Date of Patent: Dec. 17, 2019

(54) RELEASABLE ELBOW CONNECTOR

(71) Applicant: KONINKLIJKE PHILIPS N.V., Eindhoven (NL)

(72) Inventor: Matthew Answine, Apollo, PA (US)

(73) Assignee: Koninklijke Philips N.V., Eindhoven (NL)

( * ) Notice: Subject to any disclaimer, the term of this patent is extended or adjusted under 35 U.S.C. 154(b) by 721 days.

(21) Appl. No.: 14/916,050

(22) PCT Filed: Sep. 2, 2014

(86) PCT No.: PCT/IB2014/064190
§ 371 (c)(1),
(2) Date: Mar. 2, 2016

(87) PCT Pub. No.: WO2015/033263
PCT Pub. Date: Mar. 12, 2015

(65) Prior Publication Data
US 2016/0206844 A1    Jul. 21, 2016

Related U.S. Application Data

(60) Provisional application No. 61/873,013, filed on Sep. 3, 2013.

(51) Int. Cl.
*A61M 16/08* (2006.01)
*A61M 16/06* (2006.01)

(52) U.S. Cl.
CPC ........ *A61M 16/0816* (2013.01); *A61M 16/06* (2013.01); *A61M 16/0825* (2014.02); *A61M 16/0875* (2013.01)

(58) Field of Classification Search
CPC .............. A61M 16/0816; A61M 16/06; A61M 16/0875; A61M 39/10; A61M 39/1011; A61M 39/1055; A61M 2039/1027; A61M 2039/1044; A61F 2/582; B21C 37/125; E04D 2013/0833; F04B 7/0034; F04B 7/0258; Y10T 29/49444; Y10T 403/42; Y10T 403/606; Y10T 403/599; Y10T 403/7073; Y10T 403/7037
See application file for complete search history.

(56) References Cited

U.S. PATENT DOCUMENTS

2003/0196658 A1   10/2003  Ging
2006/0266365 A1   11/2006  Stallard
(Continued)

FOREIGN PATENT DOCUMENTS

WO   WO2004041342 A1   5/2004
WO   WO2007081801 A2   7/2007
(Continued)

*Primary Examiner* — Jan Christopher L Merene
*Assistant Examiner* — Cana A Gallegos
(74) *Attorney, Agent, or Firm* — Michael W. Haas

(57) ABSTRACT

An elbow connector (10,20) for use with a patient interface device (2) includes a coupling portion (11,21) structured to be inserted into an opening in the patient interface device to couple the elbow connector with the patient interface device. The coupling portion includes an upper coupling portion (11*a*) and a lower coupling portion (11*b*). The elbow connector also includes a rear surface (13). Applying pressure to the rear surface causes the upper coupling portion to move towards the lower coupling portion.

11 Claims, 4 Drawing Sheets

(56) References Cited

U.S. PATENT DOCUMENTS

| | | |
|---|---|---|
| 2009/0194111 A1 | 8/2009 | Fu |
| 2010/0024825 A1 | 2/2010 | Smith |
| 2012/0216813 A1 | 8/2012 | Matula, Jr. |
| 2014/0150798 A1* | 6/2014 | Fong ................. A61M 16/0816 128/206.21 |
| 2015/0144139 A1* | 5/2015 | Lockhart ............... A61M 16/06 128/205.25 |

FOREIGN PATENT DOCUMENTS

| | | |
|---|---|---|
| WO | WO2007143655 A2 | 12/2007 |
| WO | WO2007143792 A1 | 12/2007 |
| WO | WO2013006899 A1 | 1/2013 |
| WO | WO2013098674 A1 | 7/2013 |

* cited by examiner

RELEASABLE ELBOW CONNECTOR

CROSS-REFERENCE TO RELATED APPLICATIONS

This patent application claims the priority benefit under 35 U.S.C. § 371 of international patent application no PCT/IB2014/064190, filed Sep. 2, 2014, which claims the priority benefit under 35 U.S.C. § 119(e) of U.S. Provisional Application No. 61/873,013 filed on Sep. 3, 2013, the contents of which are herein incorporated by reference.

BACKGROUND OF THE INVENTION

1. Field of the Invention

The present invention pertains to an elbow connector for use with a patient interface device, and, in one or more particular embodiments, to an elbow connector that is configured to couple with and uncouple from the patient interface device. The present invention also pertains to a method of coupling or uncoupling an elbow connector and a patient interface device.

2. Description of the Related Art

There are numerous situations where it is necessary or desirable to deliver a flow of breathing gas non-invasively to the airway of a patient, i.e., without intubating the patient or surgically inserting a tracheal tube in their esophagus. For example, it is known to ventilate a patient using a technique known as non-invasive ventilation. It is also known to deliver positive airway pressure (PAP) therapy to treat certain medical disorders, the most notable of which is OSA. Known PAP therapies include continuous positive airway pressure (CPAP), wherein a constant positive pressure is provided to the airway of the patient in order to splint open the patient's airway, and variable airway pressure, wherein the pressure provided to the airway of the patient is varied with the patient's respiratory cycle. Such therapies are typically provided to the patient at night while the patient is sleeping.

Non-invasive ventilation and pressure support therapies as just described involve the placement of a patient interface device including a mask component having a soft, flexible cushion on the face of a patient. The mask component may be, without limitation, a nasal mask that covers the patient's nose, a nasal cushion having nasal prongs that are received within the patient's nares, a nasal/oral mask that covers the patient's nose and mouth, or a full face mask that covers the patient's face. Such patient interface devices may also employ other patient contacting components, such as forehead supports, cheek pads and chin pads. The patient interface device is connected to a gas delivery tube or conduit and interfaces the ventilator or pressure support device with the airway of the patient, so that a flow of breathing gas can be delivered from the pressure/flow generating device to the airway of the patient. It is known to maintain such devices on the face of a wearer by a headgear having one or more straps adapted to fit over/around the patient's head.

Typical patient interface devices include an elbow connector that couples the patient interface device to the gas delivery tube or conduit. In typical patient interface devices, the elbow connector is permanently coupled to the patient interface device, or is otherwise not easily uncoupled from the patient interface device. When a patient wants to get out of bed or otherwise move around, the patient usually needs to remove the entire patient interface device to do so. The patient then has to put the patient interface device back on and perform any adjustments necessary to ensure that the patient interface device is fitted to the patient properly. The process of removing and then refitting the patient interface device is inconvenient for the patient, and especially so when the patient is tired and in a dark room.

SUMMARY OF THE INVENTION

Accordingly, it is an object of the present invention to provide an elbow connector that can couple with and release from a patient interface device. This object is achieved according to one embodiment of the present invention by providing an elbow connector including an area that can be pressed to cause a coupling portion of the elbow connector to release from the patient interface device. This object is also achieved according to another embodiment of the present invention by providing a method of coupling or uncoupling an elbow connector and a patient interface device.

In one embodiment, an elbow connector for use with a patient interface device is provided and includes a coupling portion structured to be inserted into an opening in the patient interface device to couple the elbow connector with the patient interface device. The coupling portion includes an upper coupling portion and a lower coupling portion. The elbow connector also includes a rear surface. Applying pressure to the rear surface causes the upper coupling portion to move towards the lower coupling portion.

In another embodiment, a method of coupling or uncoupling an elbow connector and a patient interface device is provided and includes applying pressure to a rear surface of the elbow connector. While continuing to apply pressure to the rear surface of the elbow connector, inserting a coupling portion of the elbow connector into an opening formed in the patient interface device or removing the coupling portion of the elbow connector from the opening formed in the patient interface device, and releasing pressure from the rear surface of the elbow connector after the coupling portion of the elbow connector is fully inserted into or fully removed from the opening formed in the patient interface device.

These and other objects, features, and characteristics of the present invention, as well as the methods of operation and functions of the related elements of structure and the combination of parts and economies of manufacture, will become more apparent upon consideration of the following description and the appended claims with reference to the accompanying drawings, all of which form a part of this specification, wherein like reference numerals designate corresponding parts in the various figures. It is to be expressly understood, however, that the drawings are for the purpose of illustration and description only and are not intended as a definition of the limits of the invention.

DETAILED DESCRIPTION OF EXEMPLARY EMBODIMENTS

Figure 1:
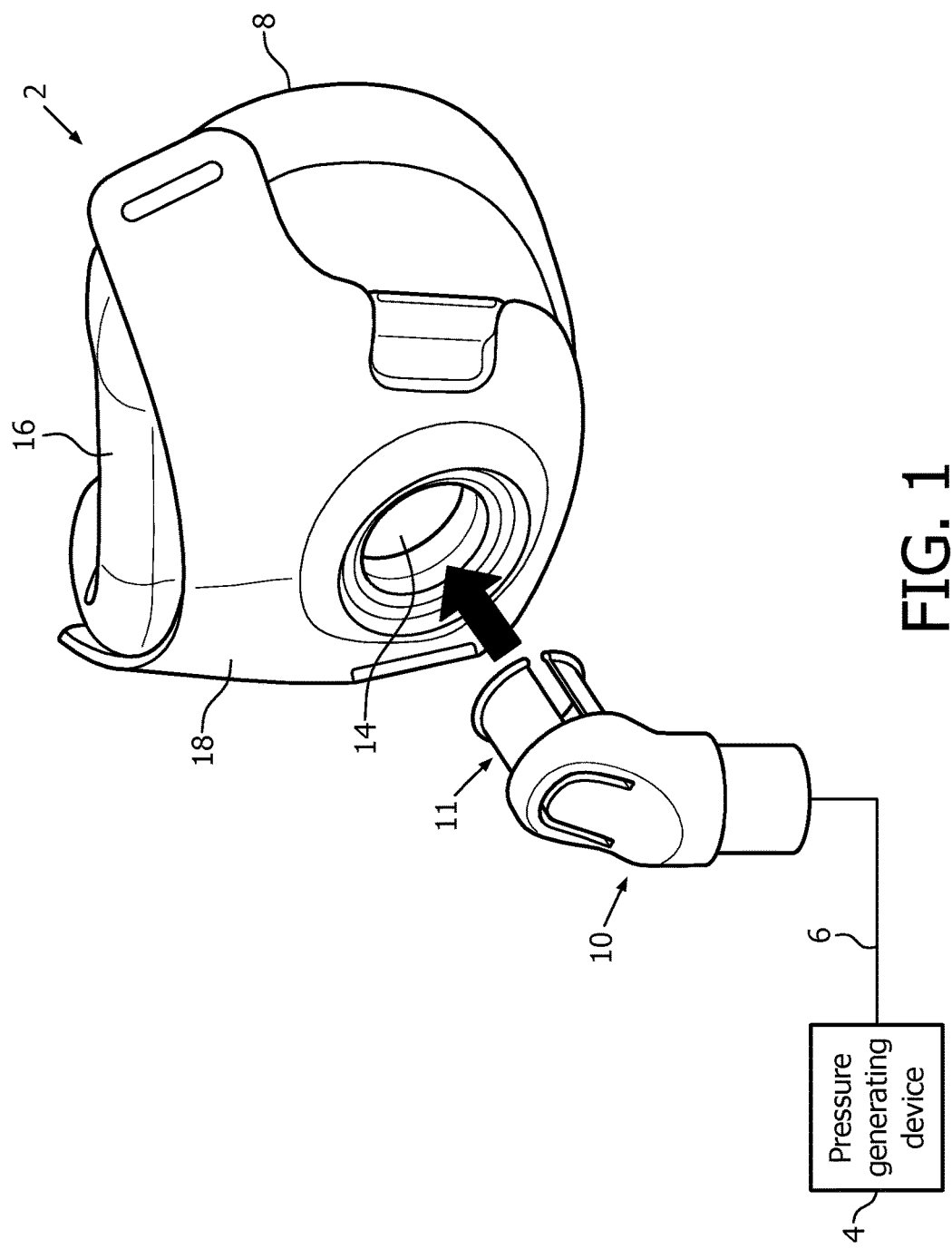
FIG. 1 is a schematic diagram of a system adapted to provide a regimen of respiratory therapy to a patient according to one exemplary embodiment of the invention.

As used herein, the singular form of "a", "an", and "the" include plural references unless the context clearly dictates otherwise. As used herein, the statement that two or more parts or components are "coupled" shall mean that the parts are joined or operate together either directly or indirectly, i.e., through one or more intermediate parts or components, so long as a link occurs. As used herein, "directly coupled" means that two elements are directly in contact with each other. As used herein, "fixedly coupled" or "fixed" means that two components are coupled so as to move as one while maintaining a constant orientation relative to each other.

As used herein, the word "unitary" means a component is created as a single piece or unit. That is, a component that includes pieces that are created separately and then coupled together as a unit is not a "unitary" component or body. As employed herein, the statement that two or more parts or components "engage" one another shall mean that the parts exert a force against one another either directly or through one or more intermediate parts or components. As employed herein, the term "number" shall mean one or an integer greater than one (i.e., a plurality).

Directional phrases used herein, such as, for example and without limitation, top, bottom, left, right, upper, lower, front, back, and derivatives thereof, relate to the orientation of the elements shown in the drawings and are not limiting upon the claims unless expressly recited therein.

A system 2 adapted to provide a regimen of respiratory therapy to a patient according to one exemplary embodiment of the disclosed concept is generally shown in FIG. 1. System 2 includes a pressure generating device 4, a delivery conduit 6, and a patient interface device 8. An elbow connector 10 is fluidly coupled to delivery conduit 6. Elbow connector 10 is shown uncoupled from patient interface device 8 in FIG. 1. However, elbow connector 10 includes a coupling portion 11 that is structured to be inserted into an opening 14 in patient interface device 8 to couple elbow connector 10 with patient interface device 8.

Pressure generating device 4 is structured to generate a flow of breathing gas and may include, without limitation, ventilators, constant pressure support devices (such as a continuous positive airway pressure device, or CPAP device), variable pressure devices (e.g., BiPAP®, Bi-Flex®, or C-Flex™ devices manufactured and distributed by Philips Respironics of Murrysville, Pa.), and auto-titration pressure support devices. Delivery conduit 6 is structured to communicate the flow of breathing gas from pressure generating device 4 to patient interface device 8.

In the illustrated embodiment, patient interface 8 is a nasal/oral mask structured to cover the nose and mouth of the patient. However, any type of patient interface device 8, such as, without limitation, a nasal mask that covers the patient's nose, a nasal cushion having nasal prongs that are received within the patient's nares, or a full face mask that covers the patient's face, which facilitates the delivery of the flow of breathing gas to, and the removal of a flow of exhalation gas from, the airway of a patient may be used while remaining within the scope of the present disclosed concept. In the embodiment shown in FIG. 1, patient interface device 8 includes a flexible cushion 16 and a rigid or semi-rigid shell 18. Straps (not shown) of a headgear component may be attached to shell 18 to secure patient interface device 8 to the patient's head. The opening 14 is formed in shell 18 and, as described above, is structured to receive coupling portion 11 of elbow connector 10 to couple elbow connector 10 with patient interface device 8. Coupling elbow connector 10 with patient interface device 8 allows the flow of breathing gas from pressure generating device 4 to be communicated to an interior space defined by shell 18 and cushion 16, and then, to the airway of a patient.

Figure 3:
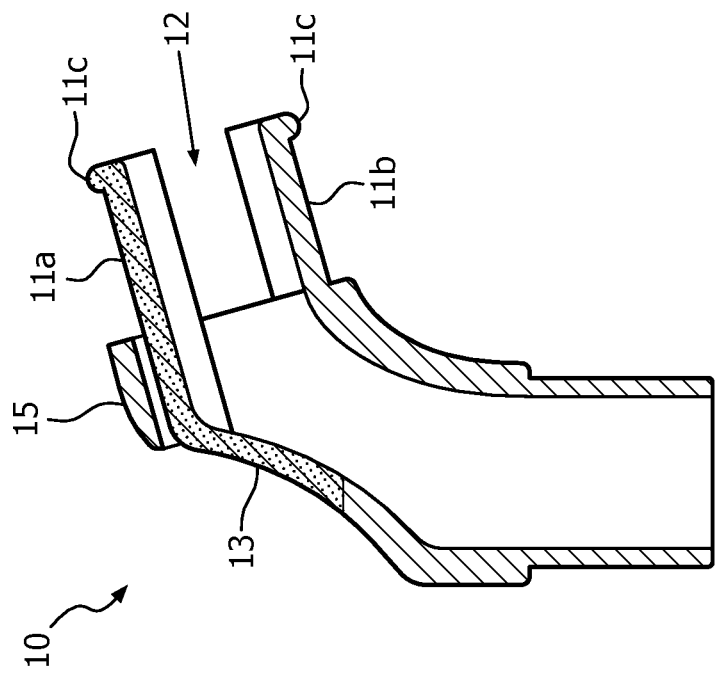
FIG. 2 is an isometric view and FIGS. 3 and 4 are side cross-sectional views of an elbow connector according to one exemplary embodiment of the invention.
Figure 2:
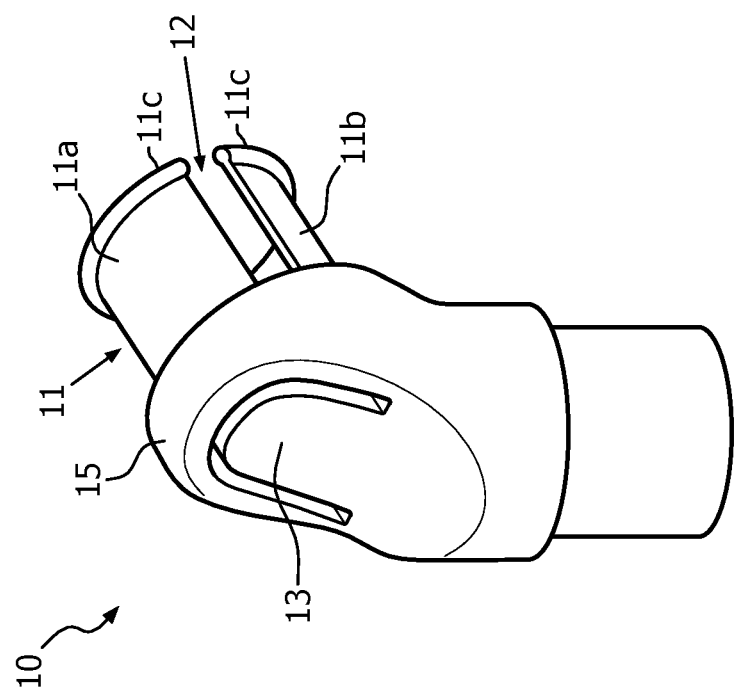
Figure 4:
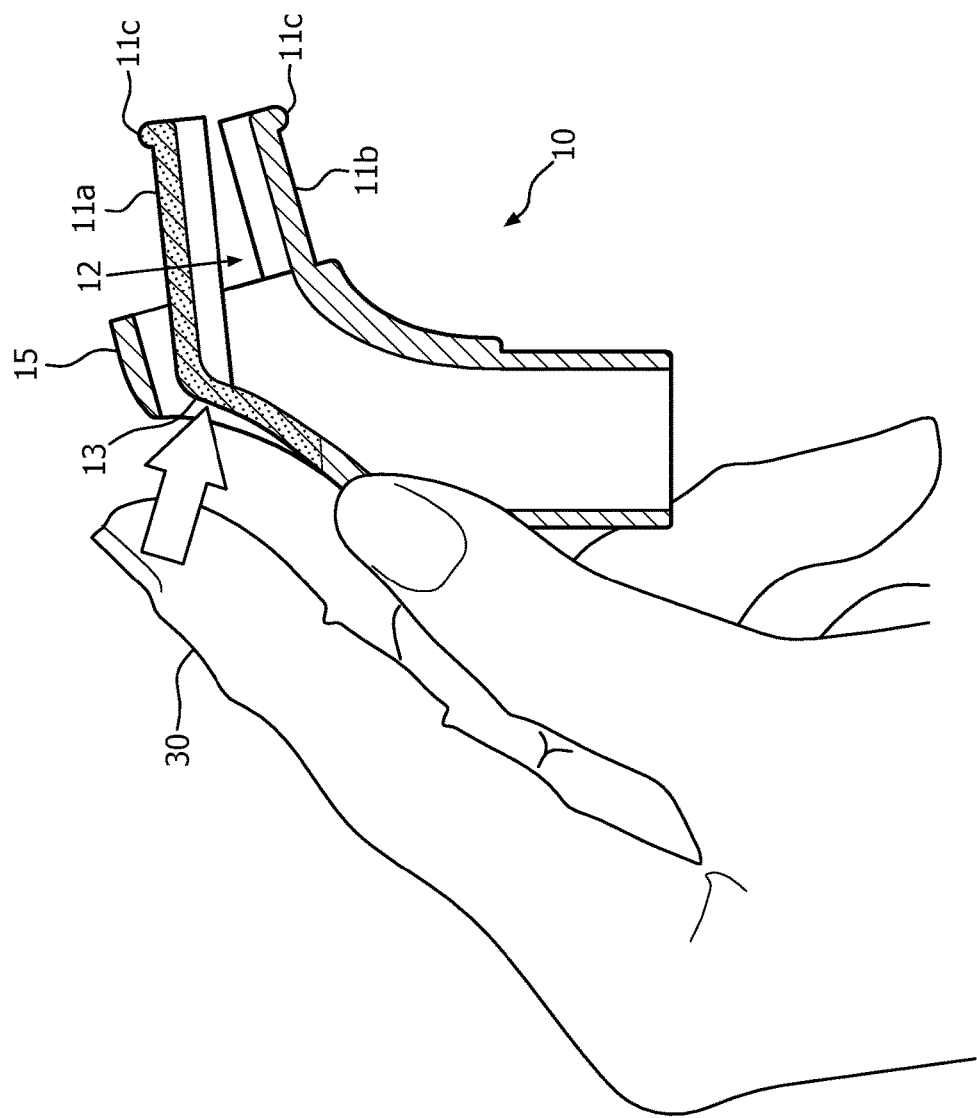

FIGS. 2-4 illustrate elbow connector 10 in accordance with one exemplary embodiment of the disclosed concept. FIG. 2 is an isometric view of elbow connector 10. FIG. 3 is a side cross-sectional view of elbow connector 10 when coupling portion 11 is in a neutral position and FIG. 4 is a side cross-sectional view of elbow connector 10 when coupling portion 11 is in a compressed position. Elbow connector 10 is configured for use with a patient interface device such as patient interface device 8 shown in FIG. 1.

Coupling portion 11 of elbow connector 10 includes an upper coupling portion 11a and a lower coupling portion 11b. A rim 11c is formed on the end portions of the upper and lower coupling portions 11a,11b that are inserted into the opening 14 in the patient interface device 8. Rim 11c is operable to hold elbow connector 10 in place when coupling portion 11 is fully inserted into the opening 14 in the patient interface device 8, thus ensuring elbow connector 10 and patient interface device 8 are securely coupled and that elbow connector 10 will not inadvertently be uncoupled from patient interface device.

A pair of slots 12 are formed between upper and lower coupling portions 11a,11b. Slots 12 allows upper coupling portion 11a to move towards lower coupling portion 11b when pressure is applied at a rear surface 13 of elbow connector 10. For example, as shown in FIG. 4, when a patient uses their finger 30 to apply pressure to rear surface 13 of elbow connector 10, upper coupling portion 11a moves towards lower coupling portion 11b, thus reducing the diameter at the end portion of coupling portion 11 that is inserted into the opening 14 of patient interface device 8.

The position of upper and lower coupling portions 11a, 11b when pressure is applied to rear surface 13 of elbow connector 10 is referred to as the compressed position. In the compressed position, the diameter of the end portion of coupling portion 11 is reduced, thus allowing coupling portion 11 to be inserted into or removed from the opening 14 in patient interface device 8. When pressure is released from rear surface 13, upper and lower coupling portions 11a,11b return to the position shown in FIG. 3 which is referred to as the neutral position. When upper and lower coupling portions 11a,11b (i.e., coupling portion 11) are in the neutral position and are fully inserted into opening 14 in patient interface device 8, elbow connector 10 is coupled with patient interface device 8 and coupling portion 11 cannot be removed from the opening 14 in patient interface device 8 until pressure is applied to rear surface 13. The coupling portion 11 (i.e., upper and lower coupling portions 11a,11b) being fully inserted into the opening 14 in patient interface device refers to the maximum amount the coupling portion 11 is intended to be inserted into the opening 14 when elbow connector 10 is coupled with patient interface device 8.

Elbow connector 10 further includes a support member 15. Support member 15 is formed above and around upper coupling portion 11a, but is not directly connected to upper coupling portion 11a. Support member 15 provides structural support for elbow connector 10. For example, support member 15 prevents upper coupling portion 11a from moving beyond the neutral position when pressure is released from rear surface 13. Furthermore, support member 15 partially surrounds rear surface 13, which causes rear surface 13 to resemble a button, thus allowing a user to conveniently identify where to press to couple or uncouple elbow connector 10 and patient interface device 8, as well as reducing the possibility of rear surface 13 inadvertently being pressed.

Rather than having to remove the entire patient interface device, as in typical patient interface device configurations, elbow connector 10 allows a patient to simply apply pressure to rear surface 13 and insert or remove coupling portion 11 from the opening 11 of patient interface device to couple or uncouple elbow connector 10 and patient interface device 8. As such, a patient does not need to entirely remove patient interface device 8 in order to disconnect patient interface device from delivery conduit 6 and pressure generating device 4.

Figure 6:
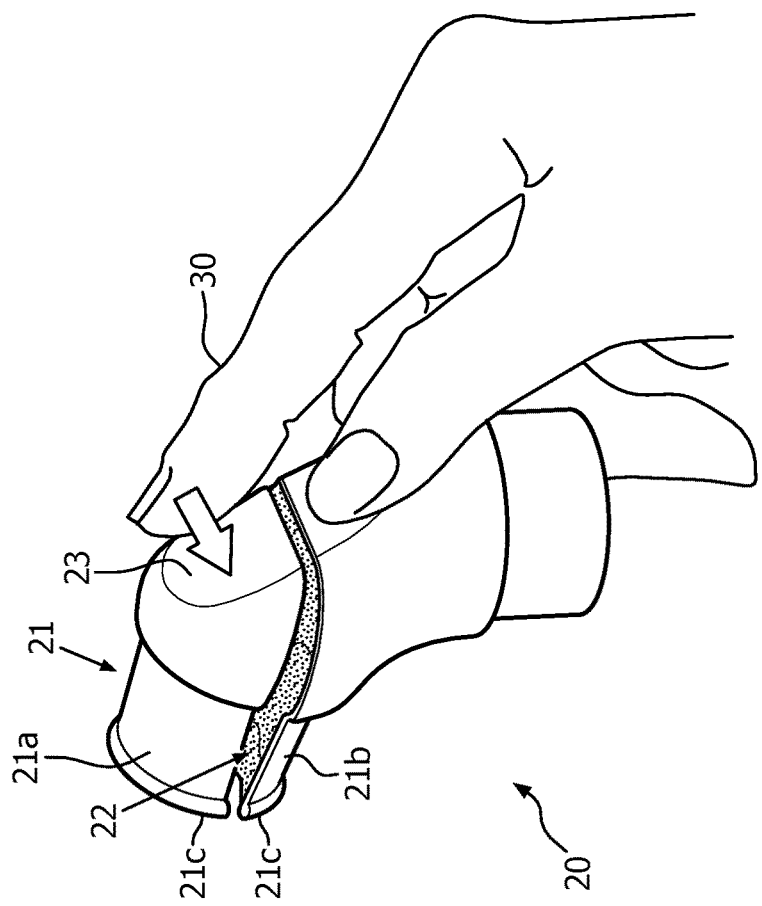
FIGS. 5 and 6 are isometric views of an elbow connector in accordance with another exemplary embodiment of the disclosed concept.
Figure 5:
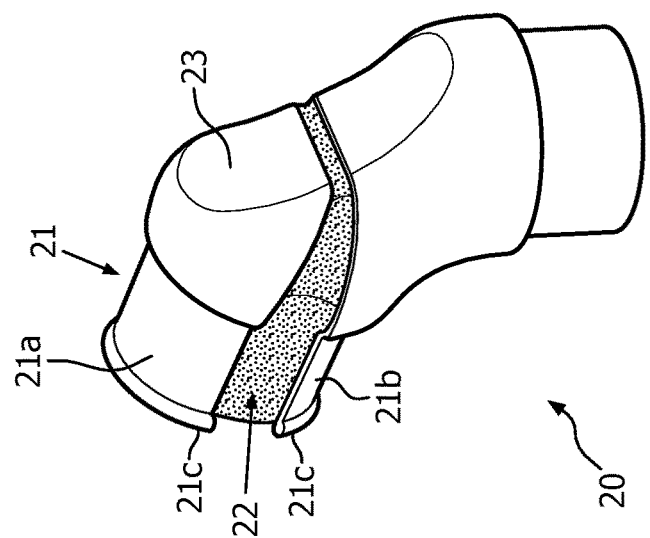

FIGS. 5-6 illustrate an elbow connector 20 in accordance with another exemplary embodiment of the disclosed concept. FIG. 5 is an isometric view of elbow connector 20 in a neutral position and FIG. 6 is an isometric view of elbow connector 20 in a compressed position.

Elbow connector 20, similar to elbow connector 10 shown in FIGS. 1-4, is structured for use with a patient interface device such as patient interface device 8 shown in FIG. 1.

Elbow connector 20 includes a coupling portion 21. Coupling portion 21 includes an upper coupling portion 21a and a lower coupling portion 21b. A rim 21c is formed on the end portions of the upper and lower coupling portions 21a,21b. Rim 21c is operable to hold elbow connector 20 in place when coupling portion 21 is fully inserted into the opening 14 in the patient interface device 8, thus ensuring elbow connector 20 and patient interface device 8 are securely coupled and that elbow connector 20 will not inadvertently release from patient interface device 8.

A flexible insert 22 is disposed between upper coupling portion 21a and lower coupling portion 21b. Upper coupling portion 21a and lower coupling portion 21b are made of a rigid material while flexible insert 22 is made of a relatively flexible material such as, for example, silicone. Flexible insert 22 allows upper coupling portion 21a to bend towards lower coupling portion 21b when pressure is applied at a rear surface 23 of elbow connector 20. For example, as shown in FIG. 6, when a patient uses their finger 30 to apply pressure to rear surface 23 of elbow connector 20, upper coupling portion 21a bends towards lower coupling portion 21b, thus reducing the diameter at the end portion of coupling portion 21 that is inserted into the opening 14 of patient interface device 8.

The position of upper and lower coupling portions 21a, 21b when pressure is applied to rear surface 23 of elbow connector 20 is referred to as the compressed position. In the compressed position, the diameter of the end portion of coupling portion 21 is reduced, thus allow coupling portion 21 to be inserted into or removed from the opening 14 in patient interface device 8. When pressure is released from rear surface 23, upper and lower coupling portions 21a,21b return to the position shown in FIG. 5 which is referred to as the neutral position. When upper and lower coupling portions 21a,21b are in the neutral position and are fully inserted into opening 14 of patient interface device 8, elbow connector 20 is coupling with patient interface device 8.

Although a support member is not shown in the exemplary embodiment illustrated in FIGS. 5-6, it will be appreciated by those having ordinary skill in the art that a support member similar to support member 15 shown in FIGS. 2-4 may be adapted for use with elbow connector 20 without departing from the scope of the disclosed concept.

The disclosed concept also provides a method of coupling or uncoupling an elbow connector and a patient interface device such as, for example, elbow connector 10 and patient interface device 8 shown in FIG. 1. The method of coupling elbow connector 10 and patient interface device 8 includes applying pressure to rear surface 13 of elbow connector 10. While continuing to apply pressure to rear surface 13, inserting coupling portion 11 into opening 14 in patient interface device 8. Then releasing pressure from rear surface 13 of elbow connector 10 after coupling portion 11 is fully inserted into patient interface device 8. The method of uncoupling elbow connector 10 and patient interface device 8 includes applying pressure to rear surface 13 of elbow connector 10. While continuing to apply pressure to rear surface 13 of elbow connector 10, removing coupling portion 11 from the opening 14 formed in patient interface device 8. Then releasing pressure from rear surface 13 of elbow connector 10 after coupling portion 11 has been fully removed from opening 14. Although a method of coupling or uncoupling an elbow connector and patient interface device has been described with respect to elbow connector 10 and patient interface device 8 shown in FIG. 1, it will be appreciated by those having ordinary skill in the art that the method may be adapted for use with any suitable elbow connector and patient interface device.

While the present invention has been described in connection with a patient interface device used to treat, for example, OSA, it will be understood that that is meant to be exemplary, and that the principles of the present invention can be can also be applied in connection with other face mask applications, such as, without limitation, anesthesia delivery masks or general use face masks where users may desire to conveniently disconnect a delivery conduit.

In the claims, any reference signs placed between parentheses shall not be construed as limiting the claim. The word "comprising" or "including" does not exclude the presence of elements or steps other than those listed in a claim. In a device claim enumerating several means, several of these means may be embodied by one and the same item of hardware. The word "a" or "an" preceding an element does not exclude the presence of a plurality of such elements. In any device claim enumerating several means, several of these means may be embodied by one and the same item of hardware. The mere fact that certain elements are recited in mutually different dependent claims does not indicate that these elements cannot be used in combination.

Although the invention has been described in detail for the purpose of illustration based on what is currently considered to be the most practical and preferred embodiments, it is to be understood that such detail is solely for that purpose and that the invention is not limited to the disclosed embodiments, but, on the contrary, is intended to cover modifications and equivalent arrangements that are within the spirit and scope of the appended claims. For example, it is to be understood that the present invention contemplates that, to the extent possible, one or more features of any embodiment can be combined with one or more features of any other embodiment.

What is claimed is:

1. An elbow connector for use with a patient interface device and a delivery conduit, comprising:
    a first coupling portion structured to be inserted into an opening in the patient interface device to couple the elbow connector with the patient interface device, the first coupling portion including an upper coupling portion and a lower coupling portion disposed opposite the upper coupling portion;
    a second coupling portion structured to couple to the delivery conduit; and an intermediate portion disposed between the first coupling portion and the second coupling portion, the intermediate portion including a rear surface, wherein the lower coupling portion includes a first end and a second end, wherein the first end of the lower coupling portion is coupled to the intermediate portion and the lower coupling portion extends in a first direction away from the intermediate portion to the second end of the lower coupling portion, wherein the rear surface faces away from the second end of the lower coupling portion, and wherein applying pressure to the rear surface in a second direction causes the upper coupling portion to move towards the lower coupling portion, wherein the second direction is toward a plane that is perpendicular to the first direction.

2. The elbow connector of claim 1, wherein the upper coupling portion and the lower coupling portion each include an end portion having a rim formed thereon.

3. The elbow connector of claim 1, further comprising a pair of slots formed between the upper coupling portion and the lower coupling portion.

4. The elbow connector of claim 1, further comprising a support member partially surrounding the rear surface and the upper coupling portion.

5. The elbow connector of claim 1, further comprising a flexible insert disposed between the upper coupling portion and the lower coupling portion.

6. The elbow connector of claim 5, wherein the upper coupling portion and the lower coupling portion are made of a rigid material and the flexible insert is made of a flexible material that is more flexible than the rigid material.

7. The elbow connector of claim 6, wherein the flexible insert is made of silicone.

8. The elbow connector of claim 5, wherein the rear surface is disposed above the flexible insert.

9. The elbow connector of claim 1, wherein while the first coupling portion is fully inserted into the opening in the patient interface device and no pressure is applied to the rear surface, the coupling portion cannot be removed from the opening in the patient interface device.

10. The elbow connector of claim 1, wherein when the upper coupling portion moves towards the lower coupling portion, a diameter of an end portion of the first coupling portion is reduced.

11. A method of coupling or uncoupling an elbow connector and a patient interface device, the elbow connector including a first coupling portion structured to be inserted into an opening in the patient interface device, a second coupling portion structured to couple with a delivery conduit, and an intermediate portion disposed between the first coupling portion and the second coupling portion, the intermediate portion including a rear surface, wherein the first coupling portion of the elbow connector includes an upper coupling portion and a lower coupling portion, wherein the lower coupling portion includes a first end and a second end, wherein the first end of the lower coupling portion is coupled to the intermediate portion and the lower coupling portion extends in a first direction away from the intermediate portion to the second end of the lower coupling portion, wherein the rear surface faces away from the second end of the lower coupling portion, the method comprising:

applying pressure to the rear surface of the elbow connector in a second direction, wherein the second direction is toward a plane that is perpendicular to the first direction, wherein applying pressure to the rear surface in the second direction causes the upper coupling portion to move towards the lower coupling portion;

while continuing to apply pressure to the rear surface of the elbow connector, inserting the first coupling portion of the elbow connector into the opening formed in the patient interface device or removing the first coupling portion of the elbow connector from the opening formed in the patient interface device; and releasing pressure from the rear surface of the elbow connector after the first coupling portion of the elbow connector is fully inserted into or fully removed from the opening formed in the patient interface device.

\* \* \* \* \*